United States Patent
Weiser et al.

(10) Patent No.: US 9,560,291 B2
(45) Date of Patent: Jan. 31, 2017

(54) AUTOMATIC IMPROVEMENT OF TRACKING DATA FOR INTRAOPERATIVE C-ARM IMAGES IN IMAGE GUIDED SURGERY

(75) Inventors: Manfred Weiser, München (DE); Rainer Lachner, München (DE)

(73) Assignee: Brainlab AG, Feldkirchen (DE)

(*) Notice: Subject to any disclaimer, the term of this patent is extended or adjusted under 35 U.S.C. 154(b) by 2391 days.

(21) Appl. No.: 11/968,671

(22) Filed: Jan. 3, 2008

(65) Prior Publication Data

US 2008/0167550 A1    Jul. 10, 2008

Related U.S. Application Data

(60) Provisional application No. 60/887,979, filed on Feb. 2, 2007.

(30) Foreign Application Priority Data

Jan. 4, 2007   (EP) .................................... 07000102

(51) Int. Cl.
*A61B 5/05*   (2006.01)
*H04N 5/32*   (2006.01)
*A61B 6/00*   (2006.01)

(52) U.S. Cl.
CPC .............. *H04N 5/32* (2013.01); *A61B 6/4441* (2013.01); *A61B 6/583* (2013.01); *A61B 90/36* (2016.02);
(Continued)

(58) Field of Classification Search
USPC ........ 600/420, 426, 427, 429; 382/103, 154, 382/128
See application file for complete search history.

(56) References Cited

U.S. PATENT DOCUMENTS 5,828,770 A    10/1998   Lies et al.
2003/0130576 A1*   7/2003   Seeley et al. ............... 600/426
(Continued)

FOREIGN PATENT DOCUMENTS

DE    197 03 556    8/1998
DE    102 15 808    11/2003
(Continued)

OTHER PUBLICATIONS

European Office Action for Application No. 07000102.9 dated Sep. 23, 2010.

*Primary Examiner* — Joel F Brutus
(74) *Attorney, Agent, or Firm* — Tucker Ellis LLP

(57) ABSTRACT

A system and method of determining a measure of accuracy of a registration mapping combining data indicative of spatial positions in a three-dimensional operating space and imaging data acquired with an imaging device located in a position and orientation in operating space is provided. A phantom is brought into a first pose, wherein the phantom is at least in partial view of the imaging device located in a second pose, the phantom comprising a marker assembly that can be imaged by the imaging device. Image data of the marker assembly of the phantom is acquired with the imaging device in the second pose. Imaged markers in the acquired image data of the marker assembly are located, and mapped markers are obtained by submitting spatial positions of the markers in the marker assembly of the phantom in the first pose to the registration mapping using the second pose as the imaging pose. A distance measure of the imaged markers and the mapped markers is determined as the measure of accuracy of the registration mapping.

19 Claims, 2 Drawing Sheets

(52) U.S. Cl.
CPC .... *A61B 2090/364* (2016.02); *A61B 2090/376* (2016.02)

(56) References Cited

U.S. PATENT DOCUMENTS

| | | | |
|---|---|---|---|
| 2006/0050988 | A1 | 3/2006 | Kraus et al. |
| 2007/0118140 | A1* | 5/2007 | Baur et al. ................... 606/87 |
| 2008/0123910 | A1* | 5/2008 | Zhu ............................. 382/128 |

FOREIGN PATENT DOCUMENTS

| | | |
|---|---|---|
| EP | 1 629 789 | 3/2006 |
| WO | 99/27839 | 8/1999 |
| WO | 00/47103 | 8/2000 |

\* cited by examiner

AUTOMATIC IMPROVEMENT OF TRACKING DATA FOR INTRAOPERATIVE C-ARM IMAGES IN IMAGE GUIDED SURGERY

RELATED APPLICATION DATA

This application claims priority of U.S. Provisional Application No. 60/887,979 filed on Feb. 2, 2007, which is incorporated herein by reference in its entirety.

FIELD OF THE INVENTION

The present invention relates to calibration of imaging devices and, more particularly, to a method and system for adjusting a registration mapping that combines data indicative of spatial positions in a three-dimensional operating space and imaging data acquired with an imaging device located in operating space.

BACKGROUND OF THE INVENTION

Image data acquired with imaging devices, preferably two-dimensional imaging devices, are often used to match or register an object, such as a body of a patient or a body portion of a patient, for example, to pre-operatively acquired spatial presentations of the object. Registration calibration of an imaging device involves the determination of parameters representing a transformation or mapping of spatial positions in a three-dimensional coordinate system or operating space to imaging data projected on a (preferably) planar imaging surface of an imaging device. The transformation or mapping is also known as registration mapping. A registration mapping of an imaging device enables the combination of image data representing two-dimensional projections of a three-dimensional object with a three-dimensional coordinate system or operating space. In image guided surgery, a spatial representation of an object, a body of a patient or a body portion of a patient may be determined in relation to a predetermined three-dimensional coordinate system or operating space.

Combinations of two-dimensional image data of an object with three-dimensional representation of that object may comprise the calibration or registration of the three-dimensional object representation relative to a coordinate system or operating space common to the imaging device and the object. The combinations also may enable the combination of image data acquired of an object in proper spatial relation to the object on a computer display, for instance. Calibration or registration of an imaging device as well as the combination of image data with object representations in a three-dimensional coordinate system or operating space can use an acquired location and orientation of the imaging device relative to the spatial coordinate system or operating space at the time of imaging the object.

A locating or tracking device may be used to determine position and orientation of an object in a three-dimensional coordinate system or operating space by means of an array of activated markers attached to the object. By receiving signals transmitted from the markers with a sensor or sensors in different spatial positions and orientations, the position and orientation of the marker array and, thus, the position and orientation of the object to which the marker array is attached may be determined. An example of a system for tracking the spatial position and angular orientation of an object may be found in U.S. Pat. No. 5,828,770.

EP 1 629 789 A1 describes a method for verifying a registration of fluoroscopic images. The accuracy of the registration is verified using a phantom with a metallic plate carrying a predetermined pattern. The phantom is tracked by a navigation or tracking system and a three-dimensional model of the phantom pattern is overlaid to an acquired image using a registration mapping, thus allowing for the visual verification of the overall registration of the acquired image. However, this method basically comprises imaging an object with a known phantom structure in a known position and orientation and overlaying a three-dimensional model of the phantom structure to the image. In this method no change or modification to the pre-calculated registration mapping can be applied.

SUMMARY OF THE INVENTION

A method of determining a measure of accuracy of a registration mapping that combines data indicative of spatial positions in a three-dimensional operating space and imaging data acquired with an imaging device located in a position and orientation in operating space and referred to as an imaging pose, may comprise the steps:
  a) bringing a phantom into a first position and orientation in operating space, referred to as first pose, where the phantom is at least in partial view of the imaging device located in a second pose, the phantom comprising an assembly of markers that can be imaged by the imaging device;
  b) acquiring image data of the marker assembly of the phantom with the imaging device in the second pose;
  c) locating imaged markers in the acquired image data of the marker assembly;
  d) obtaining mapped markers by submitting spatial positions of the markers in the marker assembly of the phantom in the first pose to the registration mapping using the second pose as imaging pose; and
  e) determining a distance measure of the imaged markers and the mapped markers as the measure of accuracy of the registration mapping.

In the method a registration mapping may be rejected if the determined measure of accuracy falls below a predetermined threshold.

A method of adjusting a registration mapping that combines data indicative of spatial positions in a three-dimensional operating space and imaging data acquired with an imaging device located in a position and orientation in operating space and referred to as an imaging pose, may comprise the steps:
  a) bringing a phantom into a first position and orientation in operating space, referred to as first pose, where the phantom is at least in partial view of the imaging device located in a second pose, the phantom comprising an assembly of markers that can be sensed by the imaging device;
  b) acquiring image data of the marker assembly of the phantom with the imaging device in the second pose;
  c) locating imaged markers in the acquired image data of the marker assembly;
  d) obtaining mapped markers by submitting spatial positions of the markers in the marker assembly of the phantom in the first pose to the registration mapping using the second pose as imaging pose;
  e) determining a distance measure of the imaged markers and the mapped markers as the measure of accuracy of the registration mapping;

f) jointly performing step g) and repeating steps d) and e) a predetermined number of times or until two consecutive measures of accuracy obtained in step e) approach one another up to a predetermined threshold or until a predetermined convergence criterion is met; and g) transforming the imaging pose used in the registration mapping to a different pose.

Step f) may comprise jointly performing step g) and repeating steps a) to e) a predetermined number of times or until two consecutive measures of accuracy obtained in step e) approach one another up to a predetermined threshold or until a predetermined convergence criterion is met.

The registration mapping may be determined by means of markers in known relative positions to the imaging device imaged with the imaging device.

A system for determining a measure of accuracy of a registration mapping that combines data indicative of spatial positions in a three-dimensional operating space and imaging data acquired with an imaging device located in a position and orientation in operating space referred to as an imaging pose, may comprise a phantom that can be brought into a first position and orientation in operating space, referred to as a first pose, where the phantom is at least in partial view of the imaging device located in a second pose, the phantom comprising an assembly of markers that can be imaged by the imaging device; a first device for acquiring image data of the marker assembly of the phantom with the imaging device in the second pose; a second device for locating imaged markers in the acquired image data of the marker assembly; a third device for obtaining mapped markers by submitting spatial positions of the markers in the marker assembly of the phantom in the first pose to the registration mapping using the second pose as imaging pose; and a fourth device for determining a distance measure of the imaged markers and the mapped markers as the measure of accuracy of the registration mapping.

The system may further comprise a fifth device for rejecting a registration mapping if the determined measure of accuracy falls below a predetermined threshold.

A system for adjusting a registration mapping that combines data indicative of spatial positions in a three-dimensional operating space and imaging data acquired with an imaging device located in a position and orientation in operating space referred to as an imaging pose may comprise a phantom that can be brought into a first position and orientation in operating space, referred to as a first pose, where the phantom is at least in partial view of the imaging device located in a second pose, the phantom comprising an assembly of markers that can be sensed by the imaging device; a first device for acquiring image data of the marker assembly of the phantom with the imaging device in the second pose; a second device for locating imaged markers in the acquired image data of the marker assembly; a third device for obtaining mapped markers by submitting spatial positions of the markers in the marker assembly of the phantom in the first pose to the registration mapping using the second pose as imaging pose; a fourth device for determining a distance measure of the imaged markers and the mapped markers as the measure of accuracy of the registration mapping; a fifth device for transforming the imaging pose used in the registration mapping to a different pose; and a sixth device for determining whether two consecutive measures of accuracy of different camera poses obtainable from the fifth device approach one another up to a predetermined threshold or until a predetermined convergence criterion is met.

In the method or system described herein, anatomical image data may be acquired before and/or after image data of the marker assembly of the phantom is acquired. Preferably a position of the anatomical structure relative to the imaging device is not changed. Further, the phantom may be manually and/or automatically brought into the first pose, and the registration mapping can be determined by means of markers in known relative positions to the imaging device and imaged by the imaging device (which may be an X-ray C-arm device).

The pose of at least one of the objects comprising the imaging device, the phantom, and an anatomical part of a patient may be acquired via a reference marker in a known position and orientation relative to the respective object by means of a position sensing system and/or a navigation system.

A marker assembly of the phantom may comprise X-ray dense and/or X-ray opaque crosses and/or other elements arranged in a predetermined pattern. Further, the elements or symbols of the marker assembly may be configured to be switched on or off to form X-ray dense and/or X-ray opaque crosses and/or other symbols. The imaged markers may be locatable with sub-pixel accuracy in the acquired image data of the marker assembly.

The imaging pose may be transformable to a different pose using a rigid body transformation.

The methods described herein may be implemented via a computer program (stored on a machine readable medium) executed on a general purpose computer, a distributed computer or a computer on a chip (SOC). The computer executing the program may function as the system in accordance with the invention.

BRIEF DESCRIPTION OF THE DRAWINGS

The forgoing and other features of the invention are hereinafter discussed with reference to the drawings.

DETAILED DESCRIPTION

Figure 1:
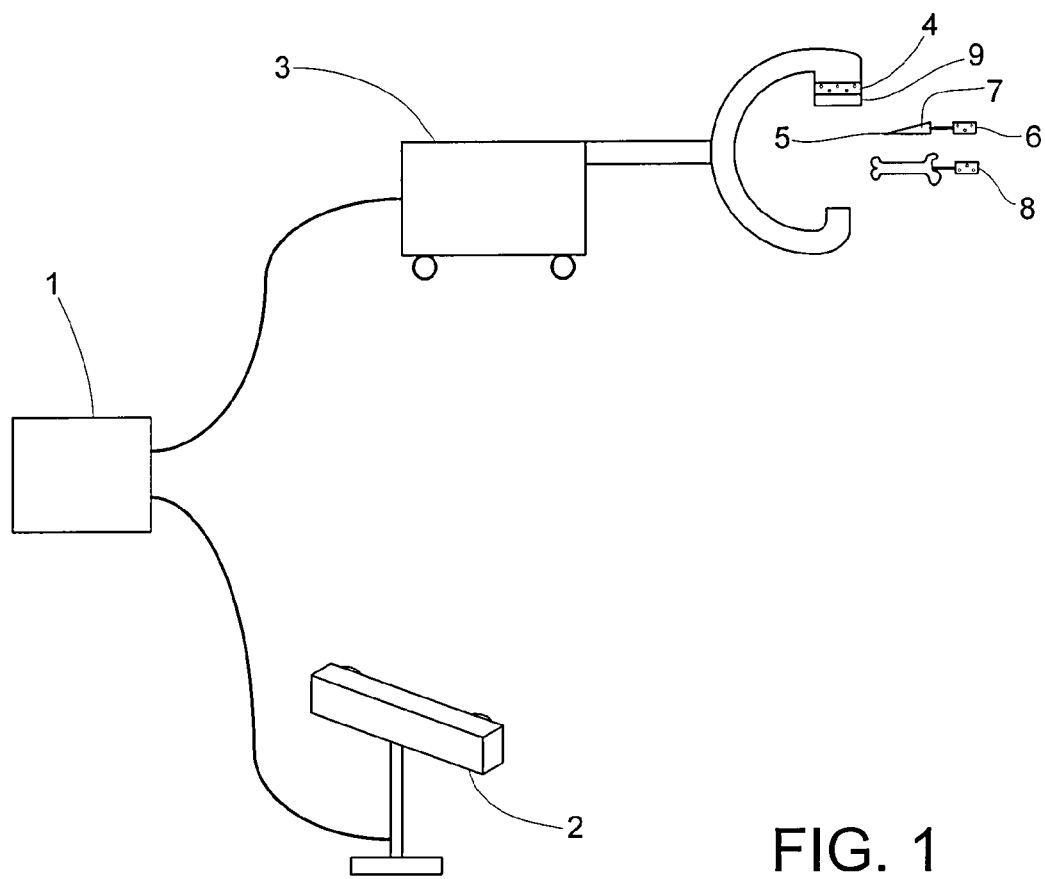
FIG. 1 is a schematic diagram of an exemplary system for adjusting a registration mapping in accordance with the invention.

FIG. 1 is a schematic diagram of an exemplary system for adjusting a registration mapping that combines data indicative of spatial positions in a three-dimensional operating space and imaging data acquired with an imaging device 3, such as an X-ray C-arm imaging device 3. A computer 1 or the like is communicatively coupled to a position sensing or tracking system 2 and to an X-ray C-arm device 3. Image data acquired by the C-arm device 3 and tracking data acquired by the tracking system 2 can be transmitted to the computer 1.

Attached to the X-ray C-arm device 3 is a reference marker array 4, which can be tracked by the position sensing or tracking system 2. An assembly of X-ray dense or opaque markers may be attached to the C-arm device 3. An accuracy assessment phantom 5 is also shown in FIG. 1. The accuracy assessment phantom 5 includes a reference marker array 6 attached thereto.

The phantom 5 carries a predetermined pattern of features 7 comprising elements or symbols made from X-ray dense material that has a predetermined spatial relation to the phantom 5. A further reference marker array may be attached to the body of a patient or a body portion of a patient, for instance, thus establishing a world coordinate system that may be used to determine the opaque space.

Figure 2:
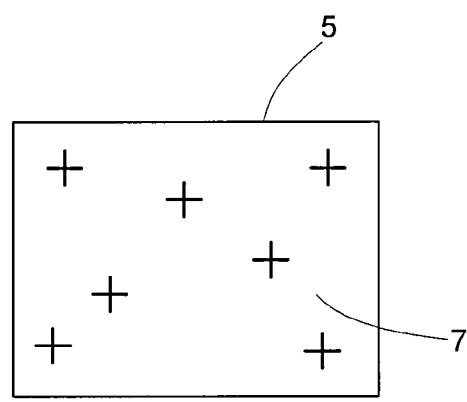
FIG. 2 illustrates an exemplary accuracy assessment phantom that may be used in accordance with the invention.

FIG. 2 illustrates an exemplary accuracy assessment phantom 5 comprising an assembly 7 of markers that can be sensed or imaged by the imaging device 3. The marker assembly 7 comprises markers arranged in a predetermined pattern of elements and/or symbols. The elements and/or symbols of marker assembly 7 may be made from X-ray dense or X-ray opaque material. The marker assembly 7 may comprise a number of crosses distributed over a predetermined planar area, but other arrangements of marker elements or assemblies are possible as described herein.

An alternative embodiment of the accuracy assessment phantom 5 may be made entirely from X-ray dense or X-ray opaque material leaving the marker elements and/or symbols transparent to X-rays or other imaging radiation. The phantom 5 may be imaged with or without the patient anatomy so that the projected or imaged pattern of marker elements is at least partially visible with the acquired image.

By performing a known calibration procedure, a registration mapping can be obtained that corrects the acquired image or image data for distortion and maps three-dimensional spatial positions in operating space or world coordinates to two-dimensional coordinates. Image calibration or registration allows the image to be used for navigation in an image guided surgery system, for instance.

If during image acquisition the positional relationship between the reference marker array 4 (which is attached to the imaging device) and the reference marker array 8 (which determines the patient world coordinate system or operating space) is inaccurately tracked, the acquired image or image data may not be usable due to an inaccurate or erroneous registration mapping. However, it may be assumed that the registration mapping derived from the tracked relation is close to the real registration relation such that it needs only a small correction to be usable. To determine the correction, the image is processed by the computer 1 by applying an image analysis search for the projected pattern of the marker symbols of the phantom.

The system and method provided herein can determine the image coordinates of the projected marker elements in the image data acquired from the phantom 5 with sub-pixel accuracy (the image coordinates may be determined with an accuracy below the unit size of a picture element or pixel). Further, from the known spatial relationship between the accuracy assessment phantom 5 and the reference marker array 6 attached to the phantom as well as from the tracked spatial relationship between the reference marker array 6 of the phantom and the reference marker array 8 attached to the anatomy of the patient, the position and orientation of the original marker elements or symbols in the marker assembly of the phantom 5 may be determined.

By means of the pre-calculated registration mapping, mapped or target positions of the crosses in the marker assembly of the phantom 5 can be determined in the image data and compared with positions found by image analysis in the image of the marker assembly of the phantom with the imaging device, the 'is-positions'. The spatial differences between the detected and the imaged or projected marker elements or crosses can be described or represented by a distance measure. Preferably the distance measure assumes non-zero and positive values.

The distance measure obtained from a comparison between detected and projected or imaged marker elements may be minimized by changing the external tracking information, e.g., the relationship between the position and orientation of the imaging device tracked via the reference marker array and the position and orientation of the patient anatomy or portions of the patient anatomy tracked via the reference marker array starting from a predetermined or 'is-position' may be changed. The external tracking information further indicates the position of a calculated focal point, e.g., the X-ray source of the X-ray C-arm device in operating space or three-dimensional world coordinates. Minimization of the distance measure of detected and projected markers of the marker assembly of the phantom may be interpreted as moving a virtual focal point starting from a calculated position of an initial registration mapping.

An adjustment of the registration mapping may be described by six parameters: three rotational and three-translational degrees of freedom describing, for example, a rigid body motion. The determination of parameters minimizing the distance measure including the adjustment of the registration mapping can be accomplished by an optimization algorithm. A minimized distance measure between the detected and projected marker elements of the marker assembly of the phantom corresponds to an optimal external relation between the position and orientation of the imaging device 3 in operating space, thus representing improved tracking information.

If the internal registration (i.e., the registration mapping or the calculation of the internal projection of the imaging device) is erroneous, the distance measure obtained by the inventive method will remain above a given threshold. This enables the quality of the overall registration accuracy achieved by means of the distance measure or the minimized distance measure to be assessed. The distance measure may be compared to a predetermined threshold representing the accuracy or quality of the registration mapping.

A user may wish to skip the accuracy determination or adjustment of a registration mapping for a view or even all images or image data with the imaging device 3

The phantom 5 may be manually or automatically removable from the imaging set-up. This may be accomplished by using a motor drive, a robotic device or any other suitable mobilizing equipment. The movement of the phantom 5 may be initiated or triggered by direct interaction with the respective device or with a navigation system.

The elements or symbols in the marker assembly of the phantom may be dynamically switched on or off to form an X-ray dense or an X-ray opaque pattern during an image acquisition process. Any suitable mechanism to accomplish dynamic formation and/or removal of marker elements or structures in a reproducible or repeatable way may be used.

Figure 3:
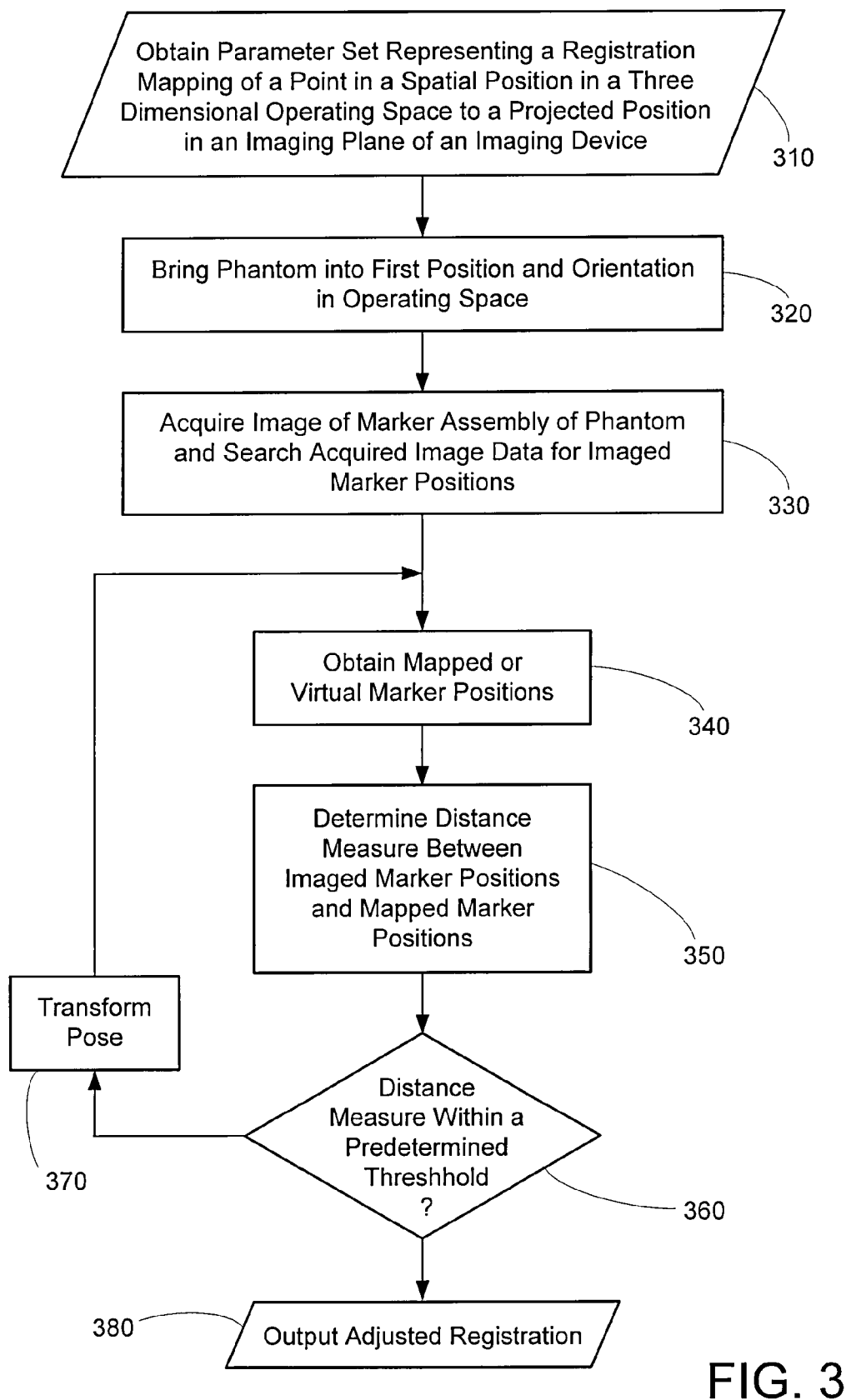
FIG. 3 is a flow diagram illustrating an exemplary method for adjusting a registration mapping in accordance with the invention.

Turning now to FIG. 3, there is shown a flow-diagram of an exemplary method for adjusting a registration mapping that combines data indicating spatial positions in a three-dimensional coordinate space or operating space and imaging data acquired with an imaging device located in operating space. Beginning at step 310, a parameter set is obtained representing a registration mapping of a point in a spatial position in a three-dimensional operating space to a projected position in an imaging plane of an imaging device 3.

In step 320 a phantom 5 is brought into a first position and orientation in operating space, so that the phantom 5 is at least in partial view of the imaging device 3, wherein the imaging device is located in a second position and orientation. The phantom 5 comprises an assembly of markers that can be sensed or imaged by the imaging device 3. Preferred embodiments of the phantom and the marker assembly are described above.

In step 330 an image of the marker assembly 7 of the phantom 5 is acquired with the imaging device 3 in the second position and orientation. Also in step 330 the acquired image data are searched for marker positions imaged of the marker assembly.

In step 340 mapped or virtual marker positions are obtained by applying the registration mapping to spatial positions of the markers in the marker assembly 7 of the phantom 5 in the first position and orientation, while using the second position and orientation as the position and orientation of the imaging device.

In step 350 a distance measure is determined between the imaged markers positions and the mapped marker positions as the measure of accuracy of the registration mapping.

In step 360 it is determined whether two consecutive measures of accuracy expressed in the distance measure of step 350 approach one another up to a predetermined threshold or whether a predetermined convergence criterion is met.

If the result of the determination is that two consecutive measures of accuracy are not approaching each other (i.e., no in step 360), the imaging pose used in the registration mapping is transformed in step 370 to a different pose, preferably using a transformation that reduces or minimizes the distance measure determined in step 350. Processing is then resumed or repeated starting with step 340. Alternatively, the processing may be resumed or repeated starting with step 320. Referring back to step 360, if the result of the determination is that two consecutive measures of accuracy are approaching each other (i.e., yes in step 360), then at step 380 the adjusted registration mapping is output as a result.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method using a system including a computer, a phantom, a tracking system and an imaging device, wherein a registration mapping is provided that combines data indicative of spatial positions in a three-dimensional operating space and imaging data acquired with the imaging device located in a second position and orientation in operating space referred to as an imaging pose, the method comprising:
a) orienting the imaging device with the phantom in a first position and orientation in the operating space, referred to as a first pose, wherein the phantom is at least in partial view of the imaging device located in a second pose, the phantom comprising a marker assembly having a plurality of markers that can be imaged by the imaging device, using X-ray dense and/or X-ray opaque crosses and/or symbols arranged in a predetermined pattern as marker elements on the marker assembly, and changing a characteristic of the marker elements to form the X-ray dense and/or X-ray opaque crosses and/or symbols;
b) acquiring by the imaging device image data of the marker assembly with the imaging device disposed in the second pose;
c) identifying by the computer imaged markers in the image data of the marker assembly acquired by the imaging device and determining by the computer first marker positions of the imaged markers identified by the computer;
d) determining by the computer second marker positions by applying the registration mapping to spatial positions of the plurality of markers of the marker assembly determined by the tracking system with the phantom in the first pose using the second pose as the imaging pose;
e) determining a distance measure of the first marker positions and the second marker positions, wherein the distance measure represents spatial differences between said first marker positions and said second marker positions by positive, non-zero values;
f) transforming the imaging pose used in the registration mapping to a different imaging pose, of the imaging device, using a rigid body transformation reducing the distance measure, if the distance measure is outside a predetermined threshold; and
g) determining whether two consecutive distance measures of the imaging poses approach one another up to the predetermined threshold or until a predetermined convergence criterion is met, thereby calibrating the imaging device.

2. The method according to claim 1, wherein the registration mapping is rejected if the distance measure exceeds a predetermined threshold.

3. The method according to claim 1, wherein bringing the phantom into the first pose includes automatically or manually bringing the phantom into the first pose.

4. The method according to claim 1, further comprising determining the registration mapping based on markers in known positions relative to the imaging device.

5. The method according to claim 1, further comprising acquiring anatomical image data before and/or after acquiring image data of the marker assembly of the phantom.

6. The method according to claim 1, wherein the imaging device is an X-ray C-arm device.

7. The method according to claim 1, further comprising acquiring a pose of at least one of the imaging device, the phantom, or an anatomical part of a patient via a reference marker in a known position and orientation relative to a respective imaging device, phantom or anatomical part via a position sensing system and/or a navigation system.

8. The method according to claim 1, wherein changing a characteristic comprises switching the X-ray dense and/or X-ray opaque crosses and/or symbols on or off to form the X-ray dense and/or X-ray opaque crosses and/or symbols arranged in a predetermined pattern.

9. The method according to claim 8, wherein switching the X-ray dense and/or X-ray opaque crosses and/or symbols on or off comprises dynamically switching the X-ray dense and/or X-ray opaque crosses and/or symbols on or off to form the X-ray dense and/or X-ray opaque crosses and/or symbols arranged in a predetermined pattern.

10. The method according to claim 1, wherein determining first marker positions includes determining first marker positions of the imaged markers with sub-pixel accuracy in the image data of the marker assembly acquired by the imaging device.

11. The method according to claim 1, wherein determining the second marker positions based on a position of the phantom includes using a medical tracking system to determine a position of the phantom.

12. A system comprising:
an imaging device located in a position and orientation in operating space and referred to as an imaging pose, said imaging device operable to acquire said imaging data;
a phantom comprising an assembly of markers that can be imaged by the imaging device, a marker assembly comprising X-ray dense and/or X-ray opaque crosses and/or symbols arranged in a predetermined pattern and configured to have a characteristic changed to form the X-ray dense and/or X-ray opaque crosses and/or symbols, wherein when the phantom is placed in a first position and orientation in operating space, referred to as a first pose, and in at least partial view of the imaging device located in a second pose, said imaging device is configured to acquire image data of the marker assembly of the phantom with the imaging device in the second pose;
a tracking system for tracking reference markers on the imaging device and/or the phantom; and
a computer system configured to
identify imaged markers in the image data of the marker assembly acquired by the imaging device and determine first marker positions of the imaged markers that have been identified,
determine second marker positions by applying a registration mapping combining data indicative of spatial positions in a three-dimensional operating space and imaging data to spatial positions of the assembly of markers in the marker assembly with the phantom in the first pose using the second pose as the imaging pose,
determine a distance measure of the first marker positions and the second marker positions, wherein the distance measure represents spatial differences between said first marker positions and said second marker positions by positive, non-zero values,
transform the imaging pose used in the registration mapping to a different imaging pose, of the imaging device, using a rigid body transformation reducing the distance measure, if the distance measure is outside a predetermined threshold, and
determine whether two consecutive distance measures of the imaging poses approach one another up to a predetermined threshold or until a predetermined convergence criterion is met, thereby calibrating the imaging device.

13. The system according to claim 12, wherein the computer system is further configured to reject the registration mapping if the distance measure exceeds a predetermined threshold.

14. The system according to claim 12, wherein the computer system is configured to determine the registration mapping based on markers in known positions relative to the imaging device.

15. The system according to claim 12, wherein the imaging device is an X-ray C-arm device.

16. The system according to claim 12, wherein the computer system is configured to acquire a pose of at least one of the imaging device, the phantom, and an anatomical part of a patient based on a reference marker in a known position and orientation relative to a respective at least one imaging device, phantom or anatomical part via a position sensing system and/or a navigation system.

17. The system according to claim 12, wherein the X-ray dense and/or X-ray opaque crosses and/or symbols of the marker assembly are configured to be switched on or off to form the X-ray dense and/or X-ray opaque crosses and/or symbols.

18. The method according to claim 17, wherein the X-ray dense and/or X-ray opaque crosses and/or symbols of the marker assembly are configured to be dynamically switched on or off to form the X-ray dense and/or X-ray opaque crosses and/or symbols.

19. The system according to claim 12, wherein the computer system is configured to locate the imaged markers with sub-pixel accuracy in the image data of the marker assembly acquired by the imaging device.

* * * * *